United States Patent [19]

Borgia et al.

[11] Patent Number: 5,201,720
[45] Date of Patent: Apr. 13, 1993

[54] SYRINGE HOLDING AND EJECTING ASSEMBLY

[76] Inventors: Joseph Borgia, 2723 Riverview Dr.; Dawn Borgia, 4611 Dominium Dr., both of Naples, Fla. 33962

[21] Appl. No.: 871,821

[22] Filed: Apr. 21, 1992

[51] Int. Cl.$^5$ .............................................. A61M 5/32
[52] U.S. Cl. .................................. 604/198; 604/232; 604/263
[58] Field of Search ............... 604/110, 192, 198, 263, 604/232

[56] References Cited

U.S. PATENT DOCUMENTS

| | | | |
|---|---|---|---|
| 1,892,993 | 1/1933 | Nevin | 604/232 X |
| 2,537,550 | 1/1951 | Roos | 604/232 |
| 2,646,798 | 7/1953 | Brown | 604/232 X |
| 2,855,931 | 10/1958 | Brown | 604/232 X |
| 4,702,739 | 10/1987 | Milorad | 604/198 |
| 4,820,275 | 4/1989 | Haber et al. | 604/198 |
| 4,863,434 | 9/1989 | Bayless | 604/198 |
| 4,894,055 | 1/1990 | Sudnak | 604/198 |
| 5,088,985 | 2/1992 | Deras | 604/192 |
| 5,116,319 | 5/1992 | van den Haak | 604/110 |
| 5,163,918 | 11/1992 | Righi et al. | 604/198 |

Primary Examiner—John D. Yasko
Assistant Examiner—Adam J. Cermak
Attorney, Agent, or Firm—Merrill N. Johnson

[57] ABSTRACT

A syringe holding and ejecting assembly which has an open ended cylindrical syringe holder with a syringe holder cap rotatable mounted on the rear end of the syringe holder and an elongated plunger slidable along the axis of the holder and its cap. The syringe holder has a spring biased cylindrical shield slidably mounted on the outside of the syringe holder. The elongated syringe filled with liquid medicant has a hypodermic needle axially mounted on its front end and a medicant-sealing piston at its rear end operated by the plunger. The syringe is designed and sized to fit into the open end of the holder and by rotation of the cap, locked into the syringe holder. Means activated by the forward movement of the plunger in administering the injection of the needle and then the medicant into a patient's body causes the shield to slide forward and lock into a position surrounding the withdrawn needle. The entire assembly can now to taken to and held over a waste disposal box. By rotation of the cap to unlock the syringe from the holder, which action will permit the used syringe from coming in contact with the potentially hazardous, recently withdrawn needle.

6 Claims, 3 Drawing Sheets

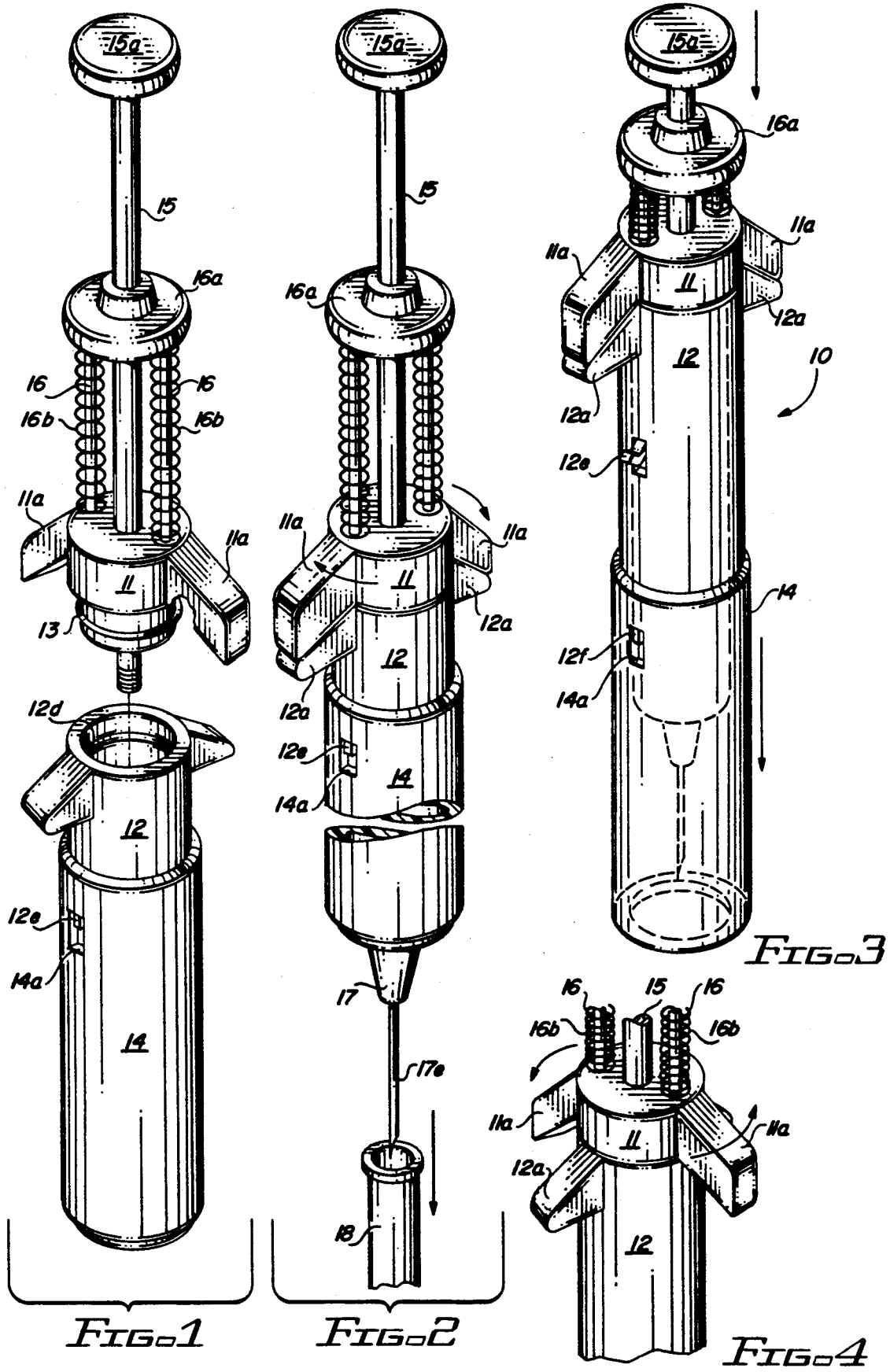

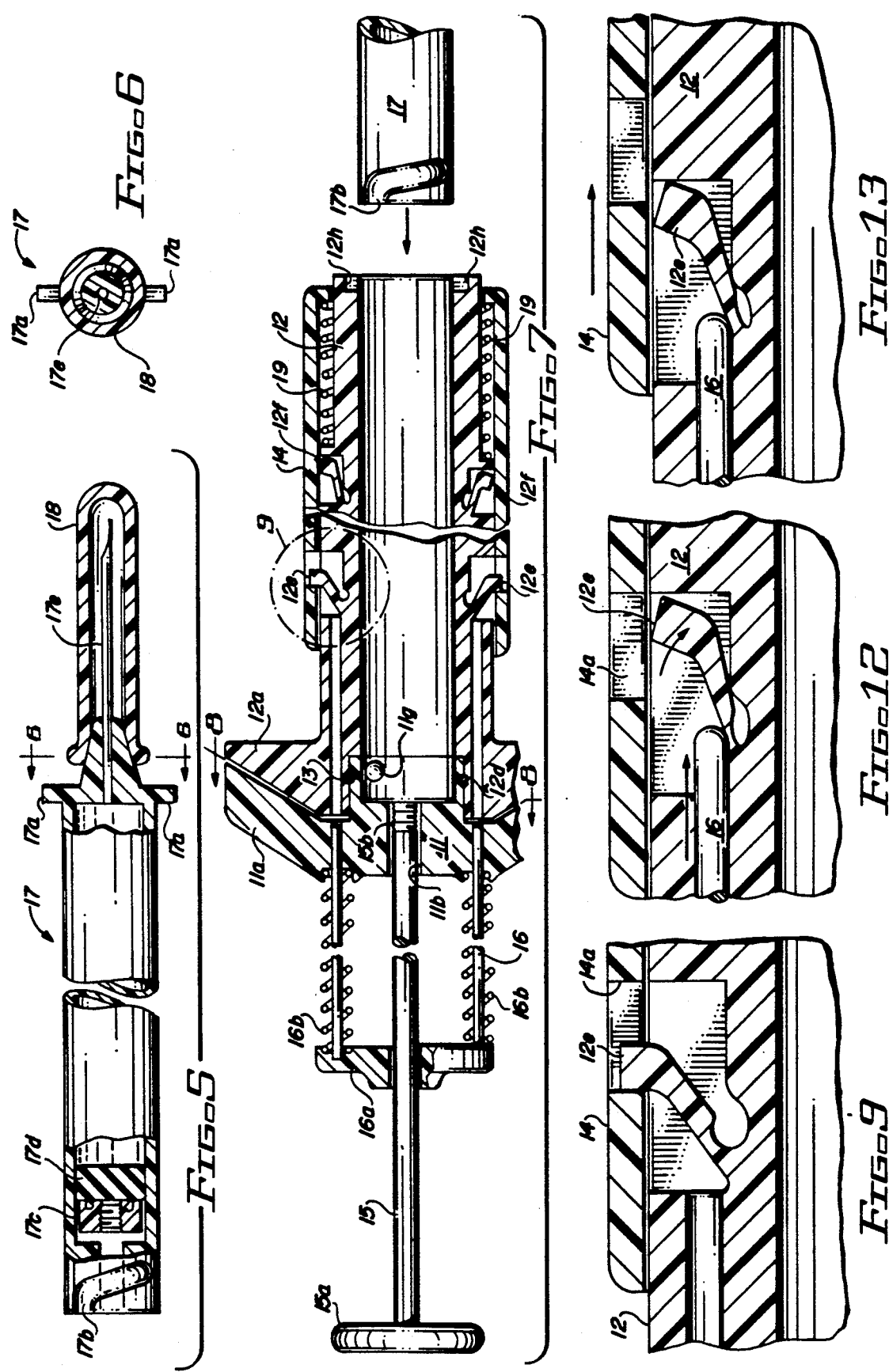

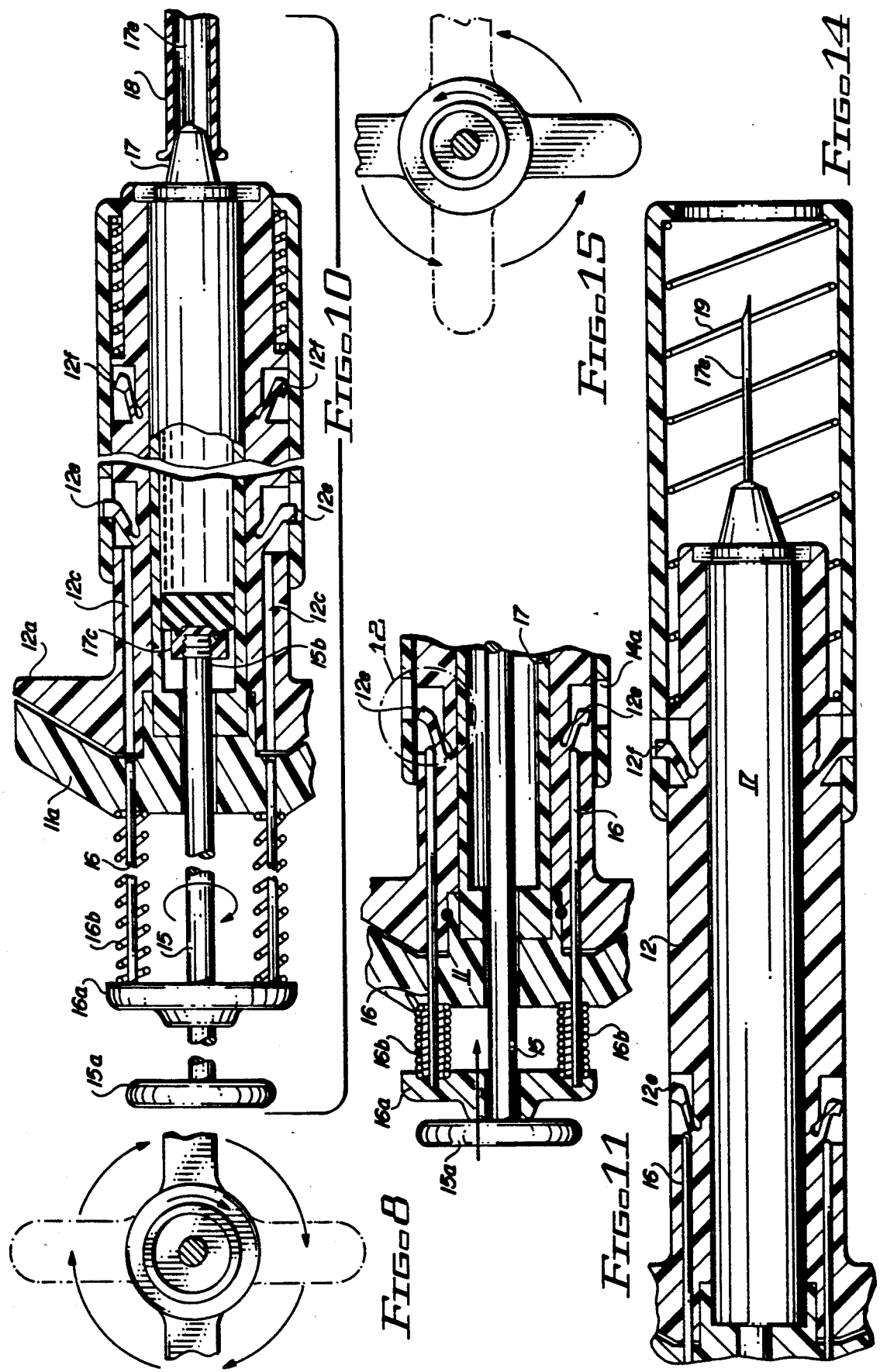

SYRINGE HOLDING AND EJECTING ASSEMBLY

BACKGROUND OF THE INVENTION

Our invention relates to the construction of a hypodermic syringe and a device for holding the syringe while the needle and the medicant within the syringe are injected into a patient and then as the needle is to be withdrawn from the patient, a shield is projected forward and locked into position around the needle to shield the needle from accidental contact until the syringe is ejected from the device into a waste container.

In today's healthcare field, nurses and other personnel are frequently required to inject patients with medicants when the patient is known to have or may have a disease, such as AIDS, which can be transmitted by the patient's blood, body secretions or tissue. Accordingly, healthcare personnell administering hypodermic injections are seriously at risk from accidental contact with a syringe needle recently withdrawn from an infected patient. Instances of serious illness and eventual death of healthcare personnel from accidental contact with infected needles are well known. Various solutions to the problem have been proposed but with limited commercial acceptance. See, for example, the syringe assemblies shown in U.S. Pat. Nos. 4,850,994 and 5,061,251.

SUMMARY OF THE INVENTION

Our invention provides a syringe holding and ejecting assembly which provides positive shielding of a recently injected syringe needle from accidental human contact.

An object of our invention is to provide a syringe which can be locked into a holding and ejecting device having a shield which is biased to slide forward and surround the syringe's needle as it is being withdrawn from a patient. The shield is locked into position surrounding the needle until the syringe and its needle are ejected from the holding device into a waste container.

Our invention simply put comprises a unique syringe holding and ejecting assembly. The assembly includes an elongated open ended cylindrical syringe holder, a syringe holder cap rotatably mounted on the rear end of the syringe holder and an elongated plunger with an externally threaded front end slidably mounted on the axis of the cap and syringe holder. The assembly also includes a cylindrical tubular shield mounted on the outside of the syringe holder and biased to slide forward of the open end of the syringe holder along a path parallel to the axis of the syringe holder.

The syringe is filled with liquid medicant and includes a sharpened hypodermic needle axially fitted onto the front end of the syringe and a liquid sealing piston at its rear end attached to a disc with an axially threaded recess. The syringe is sized to fit into the open end of the syringe holder and includes at its rear end an external groove designed to receive a hemispherical stud on the internal surface of the syringe holder cap. Rotation of the syringe holder cap locks the syringe into the syringe holder. The front end of the plunger is then screwed into the threaded recess in the syringe's disc.

Finally, the assembly includes a coiled spring activated by the forward movement of the plunger for sliding the shield forward to a position surrounding the needle as it is withdrawn from the patient into whom the needle and the medicant have been injected by the forward movement of the plunger and locking the shield in its forward position.

Preferably the means for sliding the shield forward includes a pair of spring biased push rods slidably mounted on the syringe holder cap which are driven forward by forward movement of the plunger to trigger the release of the shield to be driven forward by the coiled spring.

Other means may be used to trigger the movement of the spring biased shield and to lock the shield into its forward needle-protecting position.

BRIEF DESCRIPTION OF THE DRAWINGS

The appended drawings illustrate a preferred embodiment of our invention in which FIG. 1 is an exploded perspective view of the syringe holder, the syringe holder cap, the plunger and the slidable shield locked in its rearward position surrounding the syringe holder;

FIG. 2 is a perspective view partially broken away of the entire assembly including the syringe locked into the syringe holder;

FIG. 3 is a perspective view partially in phantom showing the plunger depressed and the shield locked into its forward needle shielding position following withdrawal of the needle from being injected into a patient;

FIG. 4 i a broken away perspective view of the syringe holder and its cap being rotated to lock a syringe into the syringe holder;

FIG. 5 is a side view partially broken away of the syringe and its removable needle cover;

FIG. 6 is a cross sectional view of the syringe taken along line 6—6 of FIG. 5;

FIG. 7 is a partially broken away cross sectional side view of the syringe holder assembly showing the end of a syringe about to be inserted into the syringe holder;

FIGS. 8 and 15 are sketches illustrating respectively the rotation of the syringe holder cap to unlock and to lock the inserted syringe into the syringe holder as seen along line 8—8 in FIG. 7;

FIGS. 9, 12 and 13 are broken away cross sectional views as seen at detail circles 9 and 12 showing respectively the locking mechanism which prevents the spring biased shield from sliding forward from its rearmost position surrounding the syringe holder, a push rod depressing the hinged flange to release the shield, and the shield moving toward its forward needle protecting position;

FIG. 10 is a partially broken away cross sectional side view of the syringe holder assembly showing the syringe locked into the syringe holder and the plunger being rotated to screw its threaded end into the disc attached to the piston of the syringe;

FIG. 11 is a detailed cross sectional side view showing the plunger being depressed and the plunger driven push rods depressing the hinged flanges to permit the shield to slide forward to its needle protecting position; and FIG. 14 is a detailed cross sectional side view showing the slide locked into its forward position surrounding the needle recently withdrawn from a patient.

DETAILED DESCRIPTION OF A PREFERRED EMBODIMENT

FIG. 1 shows the syringe holder cap 11 removed from the rear end of syringe holder 12 in order to show the O-ring 13 which fits into an semiannular groove in the lower end of cap 11 and semiannular groove 12d on the interior surface of the holder as shown in FIG. 1 to secure the rotatable joinder of holder 12 and cap 11.

FIGS. 1 and 2 also show cylindrical shield 14 locked into its rearmost position surrounding holder 12 by hinged flanges 12e, while FIG. 3 shows shield 14 of assembly 10 locked into its forward position by hinged flanges 12f so as to surround the needle of the syringe locked into holder 12.

FIGS. 1 and 2 also show plunger 15 with its cap 15a and push rods 16 and their cap 16a and springs 16b in their normal rearmost position with respect to syringe holder 12, while FIG. 3 shows plunger 15 and push rods 16 of assembly 10 in a depressed position following the injection of needle 17e and the syringe's medicant into a patient and the needle being withdrawn from the patient.

FIG. 2 also shows cap 11 having been rotated to lock syringe 17 into holder 12 and the needle cover 18 being removed from the syringe in order to inject the needle 17e into a patient.

FIG. 4 illustrates the rotational movement of cap 11 and its arms 11a to lock the inserted syringe into holder 12.

A preferred form of the syringe 17 sized to fit into the open front end of syringe holder 12 is shown in FIGS. 5 and 6. The main tubular body of syringe 17 is preferably made of a clear plastic material and contains liquid medicant to be injected into a patient through hypodermic needle 17e affixed axially to the front tapered end of the syringe.

The medicant is expelled from the syringe by forward movement of a liquid sealing piston 17d and attached disc 17c which is axially threaded to receive the end of plunger 15. As manufactured and stored, a needle-protecting cover 18 is attached to the tapered front end of the syringe, which is not removed until the content of the syringe is about to be injected into a patient.

The front end of the syringe includes two radial flanges 17a sized to fit into two radial grooves in the front end 12h of holder 12 as the syringe is inserted into holder 12. The rear end of the syringe includes an external tapered groove 17b designed to receive hemisphearical stud 11g located on the inner surface of cap 11 as shown in FIG. 7. When the cap is rotated so that its arms 11a are 90° to the arms 12a of the syringe holder as shown in FIG. 8, stud 11g will be positioned to slide into groove 17b as syringe flanges 17a are fitted into radial grooves 12h. Then by 90° rotation of cap 11 as shown in FIG. 15, stud 11g will slide into groove 17b and lock the syringe into holder 12.

With the syringe securely fitted into place, assembly 10 is complete. By rotating plunger 15 its threaded forward end 15b is screwed into the threaded recess in disc 17c of the syringe. Cover 18 can then be removed from syringe 17 and the assembly is ready to inject the needle and, by depressing plunger 15, the liquid medicant into a patient.

As the plunger is being depressed, push rods 16 will also be driven forward in channels 12c (FIG. 10) to successive positions as shown in FIGS. 9, 12 and 13 to depress hinged flanges 12e and thereby release shield 14 to slide forward by coiled spring 19 into its forward-most position as shown in FIG. 14. Upon reaching that position, outwardly biased flanges 12f will enter recesses 14a to lock shield 14 into its forward position surrounding withdrawn needle 17e.

Although not shown in the drawings, one or more studs may be molded onto the outer circumference of syringe holder 12 which are designed to fit into one or more channels in the inner surface of the shield running parallel to the axis of the shield in order to guide the slide on its forward motion so as to insure that the flanges 12f will enter recesses 14 of the shield to lock the shield into its forwardmost position.

The needle is now positively protected from any accidental contact by anyone handling assembly 10. Rotation of the plunger will release the plunger from its attachment to the syringe. The assembly can then be brought to a safe waste disposal box and held vertically with the needle pointing downward over the opening in the waste disposal box and cap 11 rotated 90° to release the cap's stud 11g from the groove 17b in the syringe, thus ejecting the entire syringe from the syringe holder to fall into the waste container.

The remainder of the assembly can then be washed or cleaned as desired and the shield released from its forward position and returned to its rearward position locked onto the syringe holder and the device is now ready to receive a new syringe and be put to further use as herein described.

While we have shown and described a preferred embodiment of our invention no limitation thereof should be implied by what has been described. Alternate means for locking the syringe into the holder, for positioning and moving the shield, and for constructing the syringe will be apparent to those skilled in the art. The scope of our invention is limited only by the appended claims.

We claim:

1. A syringe holding and ejecting assembly comprising
    an elongated open ended cylindrical syringe holder,
    a syringe holder cap rotatably mounted on the rear end of the syringe holder and having a stud on its internal front surface,
    an elongated plunger slidable along an axis of the cap and the syringe holder,
    said plunger having a threaded front end,
    a cylindrical tubular shield slidably mounted on the outside of the syringe holder,
    an elongated cylindrical syringe filled with liquid medicant, a sharpened hypodermic needle axially fitted into the front end of the syringe, and a liquid sealing piston at its rear end attached to a body with an axially threaded recess,
    the syringe being sized to fit into the open end of the syringe holder and the front end of the plunger being screwed into the threaded recess in the syringe,
    said rear end of the syringe having therein an external groove for receiving the stud of the syringe cap holder whereby rotation of the syringe cap holder will lock the syringe into the syringe holder, and
    means including a coiled spring for sliding said shield forward to a position surrounding said needle as it is being withdrawn from a body into which the needle and the medicant have been injected by forward axial movement of the plunger.

2. A syringe holding and ejecting assembly as set forth in claim 1 including means associated with said holder and said syringe for locking the shield into its forward position surrounding the withdrawn needle.

3. A syringe holding and ejecting assembly as set forth in claim 1 further including means for holding the spring loaded shield in its retracted position, in which the means for sliding the shield forward includes a pair of push rods driven forward by the forward movement of the plunger, the ends of the push rods thereby releasing said shield holding means and releasing the spring loaded shield to slide forward to surround the needle as it is withdrawn from the body.

4. A syringe holding and ejecting assembly as set forth in claim 1 in which the stud on the interior surface of the cap is hemispherical and designed to fit into the external groove in the rear end of the syringe as the cap is rotated approximately 90° to lock the syringe into the syringe holder.

5. A syringe holding and ejecting assembly as set forth in claim 1 in which the syringe holder, the syringe holder cap, the plunger and the shield are all made of high density polystyrene.

6. A syringe holding and ejecting assembly as set forth in claim 1 further comprising juxapositioned semi-annular grooves in the syringe holder and the syringe holder cap and an O-ring fitted therein, said O-ring maintaining the syringe holder and the syringe holder cap in rotatable relationship.

* * * * *